United States Patent [19]

Webb et al.

[11] Patent Number: 4,565,885

[45] Date of Patent: Jan. 21, 1986

[54] METHOD FOR PREPARING OLEFINIC SILAZANES

[75] Inventors: Jimmy L. Webb, Ballston Lake; Cathryn E. Olsen, Ballston Spa, both of N.Y.

[73] Assignee: General Electric Company, Schenectady, N.Y.

[21] Appl. No.: 743,836

[22] Filed: Jun. 12, 1985

[51] Int. Cl.[4] .............................................. C07F 7/10
[52] U.S. Cl. .................................................. 556/410
[58] Field of Search ........................................ 556/410

[56] References Cited

U.S. PATENT DOCUMENTS 3,467,686  9/1969  Creamer ............................... 556/410

Primary Examiner—Paul F. Shaver
Attorney, Agent, or Firm—William H. Pittman; James C. Davis, Jr.; James Magee, Jr.

[57] ABSTRACT

Olefinic silazanes are prepared by the reaction of an olefinic amine such as allylamine with a silazane such as dimethylaminodimethylsilane or tetramethyldisilazane, preferably in the presence of a catalytic amount of a hydrogen halide source such as dimethylchlorosilane as catalyst. The highly volatile amino compound generated as a by-product (e.g., ammonia or dimethylamine) is lost by volatilization and this furnishes at least part of the driving force for the reaction.

14 Claims, 3 Drawing Figures (I) 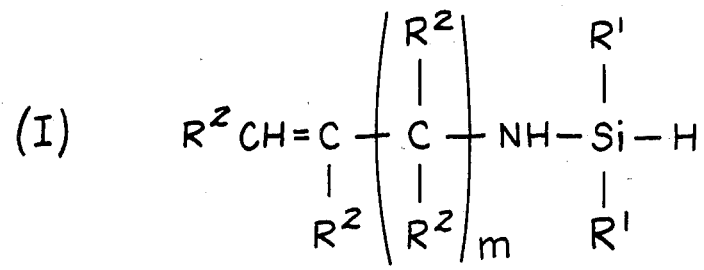
(II) 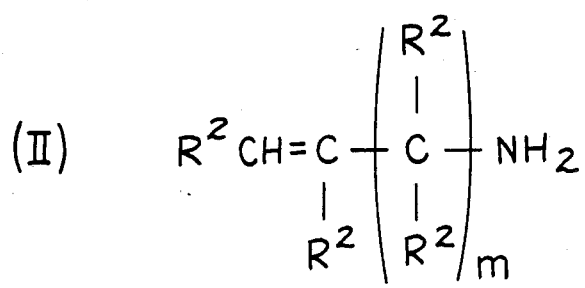
(III) 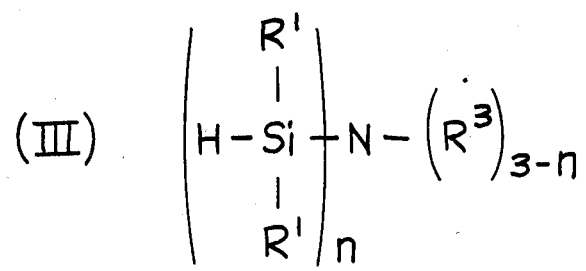

METHOD FOR PREPARING OLEFINIC SILAZANES

This invention relates to olefinic silazanes and a method for their preparation.

Olefinic silazanes are known compounds which may be used as intermediates in preparation of silylated isocyanates, as disclosed, for example, in Example 12 of U.S. Pat. No. 3,642,854. They are also useful in the preparation of bis(aminoalkyl)disiloxanes, as disclosed in copending, commonly owned applications Ser. No. 691,293, filed Jan. 14, 1985 and Ser. No. 707,630, filed Mar. 4, 1985, the disclosures of which are incorporated by reference herein.

In the method disclosed in application Ser. No. 691,293, an olefinic silazane is hydrosilated to form an intermediate which is then hydrolyzed to the bis(aminoalkyl)disiloxane. The olefinic silazane may be either a monosilazane such as 2-methyl-2-sila-3-aza-5-hexene or a disilazane such as 2-methyl-3-dimethylsilyl-2-sila-3-aza-5-hexene, but monosilazanes are strongly preferred since they yield substantially pure bis(aminoalkyl)disiloxanes rather than mixtures of isomeric compounds.

Olefinic silazanes have typically been prepared by the reaction of an olefinic amine such as allylamine with a chlorosilane such as dimethylchlorosilane in the presence of an acid acceptor. This method is disadvantageous, however, because it produces monosilazane-disilazane mixtures in which the monosilazane undergoes a relatively rapid disproportionation to the olefinic amine and disilazane. The mixture thus obtained is essentially incapable of conversion to pure bis(aminoalkyl)disiloxanes.

A principal object of the present invention, therefore, is to provide a method for preparing olefinic monosilazanes of higher purity than those obtainable from chlorosilanes.

A further object is to prepare olefinic monosilazanes by a relatively simple method, in a form which is highly suitable for conversion to relatively pure bis(aminoalkyl)disiloxanes.

Other objects will in part be obvious and will in part appear hereinafter.

In its broadest sense, the present invention is a method for preparing a composition comprising an olefinic silazane of formula I in the drawings, wherein $R^1$ and each $R^2$ is independently a $C_{1-4}$ primary or secondary alkyl radical, phenyl or substituted phenyl and m is from 1 to about 20, which comprises reacting an olefinic amine of formula II with a silazane of formula III, wherein $R^3$ is hydrogen or methyl and n is 1 or 2, with removal of the highly volatile amino compound $(R^3)_{3-n}NH_n$.

In the silazane of formula III (hereinafter sometimes designated "silazane reactant"), the $R^1$ values may be phenyl radicals; substituted phenyl radicals wherein the substituents do not react deleteriously during the practice of the invention, such as tolyl, chlorophenyl, carbomethoxyphenyl or cyanophenyl; or (preferably) $C_{1-4}$ primary or secondary alkyl radicals such as methyl, ethyl, 1-propyl, 2-propyl, 1-butyl, 2-butyl and 2-methyl-1-propyl. Methyl and ethyl radicals, especially methyl, are particularly preferred. The value of n may be 1 or 2; that is, the silazane reactant may be a mono- or disilazane.

Each $R^3$ value may be hydrogen or methyl. Thus, the amino compound produced as a by-product in the reaction may be ammonia, methylamine or dimethylamine. The preferred silazane reactants are dimethylaminodimethylsilane, wherein $R^1$ and each $R^3$ are methyl and n is 1, and tetramethyldisilazane, wherein $R^1$ is methyl, $R^3$ is hydrogen and n is 2. Tetramethyldisilazane is particularly preferred.

The $R^2$ values in the olefinic amine are usually all hydrogen. Any of them may, however, be phenyl, substituted phenyl or $C_{1-4}$ primary or secondary alkyl radicals such as those described hereinabove with respect to $R^1$, with the same preferences. It should be noted that the present invention contemplates the use of compounds wherein all $R^2$ values are the same, as well as compounds wherein they are all different. This includes compounds in which m is up to about 20 and all of the $R^2$ substituents on the resulting alkylene radical are different. The value of m is usually 1 or 2 and preferably 1. Allylamine is a particularly preferred olefinic amine.

In the method of this invention, the silazane reactant and olefinic amine are typically reacted at a temperature within the range of about 10°–100° C., preferably about 40°–100° C. Especially when the olefinic amine is allylamine, it is frequently convenient to conduct the reaction under reflux. The boiling point of allylamine is about 57° C. and the temperature rises from this level as the amine is consumed. The proportions of reagents are generally from about stoichiometric to about a 20% excess of amine. As will be apparent, the stoichiometric molar ratio of amine to silazane reactant is 1:1 in the case of a monosilazane and 2:1 in the case of a disilazane.

If desired, a substantially inert diluent such as tetrahydrofuran, dioxane, benzene, toluene, chlorobenzene, dimethylformamide or dimethyl sulfoxide may be employed. However, a diluent is generally not needed and no benefit ordinarily attaches to its use.

In a preferred embodiment of the invention, the reaction is conducted in the presence of a catalytic amount of at least one hydrogen halide source wherein the halogen has an atomic weight above 30. Thus, suitable hydrogen halides are hydrogen chloride, hydrogen bromide and hydrogen iodide; hydrogen chloride is preferred because of its high catalytic activity and relatively low cost. While not necessary, such a catalyst generally causes a substantial increase in reaction rate.

The hydrogen halide source may be the hydrogen halide itself, or it may be another active halide such as an acyl halide or a halosilane. Chlorosilanes such as dimethylchlorosilane are often useful. The amount of catalyst is generally about 0.001–0.01 milliequivalent per equivalent of silazane reactant. (For the purposes of this invention, the equivalent weight of a chlorosilane is its molecular weight divided by the number of chlorine atoms therein, and the equivalent weight of a silazane is its molecular weight divided by the number of silicon atoms therein.)

The reaction generates as a by-product a highly volatile amino compound which may be ammonia, methylamine or dimethylamine depending on the identity of the silazane reactant. The loss of said amino compound serves, at least in part, as a driving force for the reaction. An additional driving force in the case of allylamine and tetramethyldisilazane, at least, is the difference in basic strength between the by-product ammonia (weaker) and reactant allylamine (stronger).

The reaction is essentially complete when no further evolution of ammonia, methylamine or dimethylamine is noted. The product generally contains a major proportion of the desired olefinic monosilazane. It may also contain minor amounts of the corresponding disilazane and unreacted olefinic amine. If necessary, monosilazane may be purified by conventional methods such as distillation and column chromatography. It has been found that, while pure monosilazane undergoes disproportionation as described hereinabove, the rate thereof is substantially lower than that of the monosilazane in a monosilazane-disilazane mixture.

The analyses of the products obtained according to this invention were conducted by a combination of gas chromatography and mass spectrography. The gas chromatography was performed using a Varian Model 3700 chromatograph equipped with a J&W Scientific Type DB-1 glass capillary column, 30 meters in length and having an internal diameter of 0.25 mm. and a film thickness of 0.10 mm. The pressure across the capillary column was reduced with a 1/50-volume gas splitter, with the volume being made up at the end of the column before the detector. The inlet pressure was 12 psi. of helium. Thermal programming was maintained at −20° C. for 2 minutes, and then increased by 5° per minute to a final temperature of 300° C. Sample size was 0.5 microliter.

Under these conditions, the following retention times were observed:

| Compound | Retention time, sec. |
| --- | --- |
| 2-Methyl-2-sila-3-aza-5-hexene | 800 |
| 2-Methyl-3-dimethylsilyl-2-sila-3-aza-5-hexene | 1250 |

The method of this invention is illustrated by the following examples.

EXAMPLE 1

A mixture of 66.6 grams (0.5 mole) of tetramethyldisilazane, 61.6 grams (1.1 moles) of allylamine and 0.5 microliter of dimethylchlorosilane was heated under reflux for about 2 hours, during which period the reflux temperature increased from 57° to 81.5° C. Ammonia was lost by volatilization during the refluxing period. The product was immediately analyzed by gas chromatography and was found to comprise 74% 2-methyl-2-sila-3-aza-5-hexene, 18.4% 2-methyl-3-dimethylsilyl-2-sila-3-aza-5-hexene and 7.6% tetramethyldisilazane.

EXAMPLE 2

The procedure of Example 1 is repeated, except that the tetramethyldisilazane is replaced by 131.2 grams (1 mole) of dimethylaminodimethylsilane. A similar product is obtained.

The method of this invention offers several potential advantages over the chlorosilane method. For example, the production of a highly volatile material as the sole by-product permits isolation procedures to be simpler than when an amine hydrochloride is produced. Also, the monosilazane product may be more easily obtained in a form which is less susceptible to disproportionation.

What is claimed is:

1. A method for preparing a composition comprising an olefinic silazane of formula I in the drawings, wherein $R^1$ and each $R^2$ is independently a $C_{1-4}$ primary or secondary alkyl radical, phenyl or substituted phenyl and m is from 1 to about 20, which comprises reacting an olefinic amine of formula II with a silazane of formula III, wherein $R^3$ is hydrogen or methyl and n is 1 or 2, with removal of the highly volatile amino compound $(R^3)_{3-n}NH_n$.

2. A method according to claim 1 wherein m is 1 or 2 and each $R^2$ is hydrogen.

3. A method according to claim 2 wherein the reaction temperature is in the range of about 40°–100° C.

4. A method according to claim 3 wherein $R^1$ is methyl and m is 1.

5. A method according to claim 4 wherein the reaction is conducted under reflux and in the absence of diluents.

6. A method according to claim 5 wherein n is 2 and $R^3$ is hydrogen.

7. A method according to claim 5 wherein n is 1 and each $R^3$ is methyl.

8. A method according to claim 3 wherein the reaction is conducted in the presence of a catalytic amount of at least one hydrogen halide source wherein the halogen has an atomic weight above 30.

9. A method according to claim 8 wherein the amount of hydrogen halide source is about 0.001–0.01 milliequivalent per equivalent of silazane reactant.

10. A method according to claim 9 wherein $R^1$ is methyl and m is 1.

11. A method according to claim 10 wherein the reaction is conducted under reflux and in the absence of diluents.

12. A method according to claim 11 wherein the hydrogen halide source is dimethylchlorosilane.

13. A method according to claim 12 wherein n is 2 and $R^3$ is hydrogen.

14. A method according to claim 12 wherein n is 1 and each $R^3$ is methyl.

* * * * *